(12) United States Patent
Higaki et al.

(10) Patent No.: US 11,398,165 B2
(45) Date of Patent: Jul. 26, 2022

(54) SIMULATOR, INJECTION DEVICE OR IMAGING SYSTEM PROVIDED WITH SIMULATOR, AND SIMULATION PROGRAM

(71) Applicants:HIROSHIMA UNIVERSITY, Hiroshima (JP); NEMOTO KYORINDO CO., LTD., Tokyo (JP)

(72) Inventors: Toru Higaki, Hiroshima (JP); Kazuo Awai, Hiroshima (JP); Yuko Nakamura, Hiroshima (JP); Kazumasa Masuda, Tokyo (JP); Koji Yuba, Tokyo (JP); Shigeru Nemoto, Tokyo (JP)

(73) Assignees: HIROSHIMA UNIVERSITY, Hiroshima (JP); NEMOTO KYORINDO CO., LTD., Tokyo (JP)

( * ) Notice: Subject to any disclaimer, the term of this patent is extended or adjusted under 35 U.S.C. 154(b) by 472 days.

(21) Appl. No.: 16/042,274

(22) Filed: Jul. 23, 2018

(65) Prior Publication Data
US 2019/0012932 A1 Jan. 10, 2019

(30) Foreign Application Priority Data

Jul. 4, 2017 (JP) .............................. JP2017-130873

(51) Int. Cl.
*G09B 23/28* (2006.01)
*A61B 6/00* (2006.01)
(Continued)

(52) U.S. Cl.
CPC ............ *G09B 23/286* (2013.01); *A61B 6/481* (2013.01); *A61B 8/481* (2013.01); *A61M 5/007* (2013.01);
(Continued)

(58) Field of Classification Search
CPC ...... G09B 23/286; G16H 20/17; G16H 30/20; G16H 40/60; G01R 33/5601;
(Continued)

(56) References Cited

U.S. PATENT DOCUMENTS 5,583,902 A 12/1996 Bae
5,687,208 A * 11/1997 Bae ........................ G16H 20/17
378/8
(Continued)

FOREIGN PATENT DOCUMENTS

JP 2000-506398 A 5/2000
WO 97/12550 A1 4/1997
WO 2016/084373 A1 6/2016

OTHER PUBLICATIONS

Kyongtae T. Bae, "Intravenous Contrast Medium Administration and Scan Timing at CT: Considerations and Approaches", Jul. 2010, Radiology, vol. 256 No. 1, 32-61 (Year: 2010).*
(Continued)

*Primary Examiner* — Patricia J Park
*Assistant Examiner* — Adil Partap S Virk
(74) *Attorney, Agent, or Firm* — Studebaker & Brackett PC

(57) ABSTRACT

The simulator includes a chemical liquid information acquisition section configured to acquire an amount of contrast medium, a target value acquisition section configured to acquire a target duration for which a target pixel value is maintained, a protocol acquisition section configured to acquire a contrast medium injection protocol, and a prediction section for determining a predicted duration, the prediction section configured to simulate the time-dependent change in the pixel value in the tissue of the subject based on the injection protocol and the amount of the contrast medium, and the prediction section compares the predicted duration with the target duration to re-simulate, in a case
(Continued)

where the predicted duration is shorter than the target duration, the time-dependent change in a condition where a greater amount of the contrast medium than the amount of the contrast medium used in the simulation is injected to redetermine the predicted duration, and in a case where the predicted duration is longer than the target duration, the time-dependent change in a condition where a smaller amount of the contrast medium than the amount of the contrast medium used in the simulation is injected to redetermine the predicted duration.

12 Claims, 7 Drawing Sheets

(51) Int. Cl.
    *G01R 33/56*     (2006.01)
    *A61M 5/00*     (2006.01)
    *A61B 8/08*     (2006.01)
    *G16H 20/17*     (2018.01)
    *A61M 5/145*     (2006.01)
    *G16H 30/20*     (2018.01)
    *G16H 40/60*     (2018.01)
    *A61B 8/00*     (2006.01)

(52) U.S. Cl.
    CPC ....... *A61M 5/1456* (2013.01); *G01R 33/5608* (2013.01); *G16H 20/17* (2018.01); *G16H 30/20* (2018.01); *G16H 40/60* (2018.01); *A61B 6/463* (2013.01); *A61B 6/465* (2013.01); *A61B 6/54* (2013.01); *A61B 8/463* (2013.01); *A61B 8/465* (2013.01); *A61B 8/54* (2013.01); *A61M 2205/3576* (2013.01); *A61M 2205/502* (2013.01); *A61M 2205/6072* (2013.01); *G01R 33/5601* (2013.01)

(58) Field of Classification Search
    CPC . G01R 33/5608; A61M 5/1456; A61M 5/007; A61M 2205/502; A61M 2205/3576; A61M 2205/6072; A61M 2005/14292; A61M 2005/14288; A61B 6/481; A61B 8/481; A61B 6/463; A61B 6/465; A61B 8/465; A61B 8/54; A61B 6/54; A61B 8/463; A61B 34/00
    See application file for complete search history.

(56) References Cited

U.S. PATENT DOCUMENTS

| | | | |
|---|---|---|---|
| 2003/0216643 A1* | 11/2003 | Zatezalo | A61M 5/16827 600/432 |
| 2006/0127309 A1* | 6/2006 | Raffel | C07C 279/06 424/1.11 |
| 2007/0282263 A1* | 12/2007 | Kalafut | G16H 40/63 604/131 |
| 2010/0114064 A1* | 5/2010 | Kalafut | A61B 5/411 604/508 |
| 2010/0292570 A1* | 11/2010 | Tsukagoshi | A61B 6/504 600/431 |
| 2015/0227704 A1* | 8/2015 | Laster | G06F 19/3468 702/19 |
| 2015/0332455 A1* | 11/2015 | Kobayashi | A61B 6/504 382/131 |
| 2017/0281278 A1 | 10/2017 | Higaki et al. | |

OTHER PUBLICATIONS

Kazuo Awai et al., "Simulation of Aortic Peak Enhancement on MDCT Using a Contrast Material Flow Phantom: Feasibility Study", Feb. 2006 (Year: 2006).*

An Office Action; "Notice of Reasons for Refusal," mailed by the Japanese Patent Office dated May 6, 2021, which corresponds to Japanese Patent Application No. 2017-130873 and is related to U.S. Appl. No. 16/042,274 with English language translation.

* cited by examiner

SIMULATOR, INJECTION DEVICE OR IMAGING SYSTEM PROVIDED WITH SIMULATOR, AND SIMULATION PROGRAM

BACKGROUND OF THE INVENTION

Field of the Invention

The present invention relates to a simulator that simulates a time-dependent change in the pixel value in a tissue, an injection device or an imaging system provided with the simulator, and a simulation program.

Description of the Related Art

There has been a proposed simulator that predicts a time-dependent change in the pixel value in a tissue of a subject. International Publication No. WO2016/084373 describes a simulator including a prediction section that predicts, based on subject information, an injection protocol, and tissue information, a time-dependent change in the pixel value of each of a plurality of compartments produced by dividing a tissue along the blood flow direction.

SUMMARY OF THE INVENTION

The simulator descried in International Publication No. WO2016/084373 is not intended to use an injection protocol that maintains a target pixel value over a target duration.

To solve the problem described above, a simulator as an example of the present invention includes a chemical liquid information acquisition section configured to acquire an amount of contrast medium, a target value acquisition section configured to acquire a target duration for which a target pixel value is maintained, a protocol acquisition section configured to acquire a contrast medium injection protocol, and a prediction section for determining a predicted duration, the prediction section configured to simulate a time-dependent change in a pixel value in a tissue of a subject based on the injection protocol and the amount of the contrast medium, wherein the prediction section compares the predicted duration with the target duration to re-simulate, in a case where the predicted duration is shorter than the target duration, the time-dependent change in a condition where a greater amount of the contrast medium than the amount of the contrast medium used in the simulation is injected to redetermine the predicted duration, and in a case where the predicted duration is longer than the target duration, the time-dependent change in a condition where a smaller amount of the contrast medium than the amount of the contrast medium used in the simulation is injected to redetermine the predicted duration.

The simulator can simulate a time-course change in the pixel value in a tissue of a subject in a case where an injection protocol that maintains a target pixel value over a target duration is used.

Further features of the present invention will become apparent from the following description of exemplary embodiments with reference to the attached drawings.

DESCRIPTION OF THE EMBODIMENTS

Exemplary embodiments for implementing the present invention will be described below in detail with reference to the drawings. It is, however, noted that the dimensions, materials, shapes, and relative positions of components described in the following embodiments are arbitrarily determined and can be changed according to the configuration of a device to which the present invention is applied and a variety of other conditions. Further, except where particularly described, the scope of the present invention is not limited to the embodiments that will be specifically described below.

Unless otherwise particularly stated, the term "contrast medium" includes not only the contrast medium alone but the contrast medium and a chemical liquid containing a solvent and an additive different from the contrast medium. In the following description, unless otherwise particularly stated, the term "pixel value" includes a CT value, the sum or average of CT values of pixels contained in a region of interest (ROI), or an SD value (standard deviation value) in the region of interest in an imaged site having been contrasted. Further, the pixel value includes a value obtained by subtracting a value in an imaged site that has not been contrasted (CT value in imaged site in simple CT, for example) from any of the values described above. The region of interest can be set in advance, or a user can select a region of interest.

First Embodiment

Figure 1:
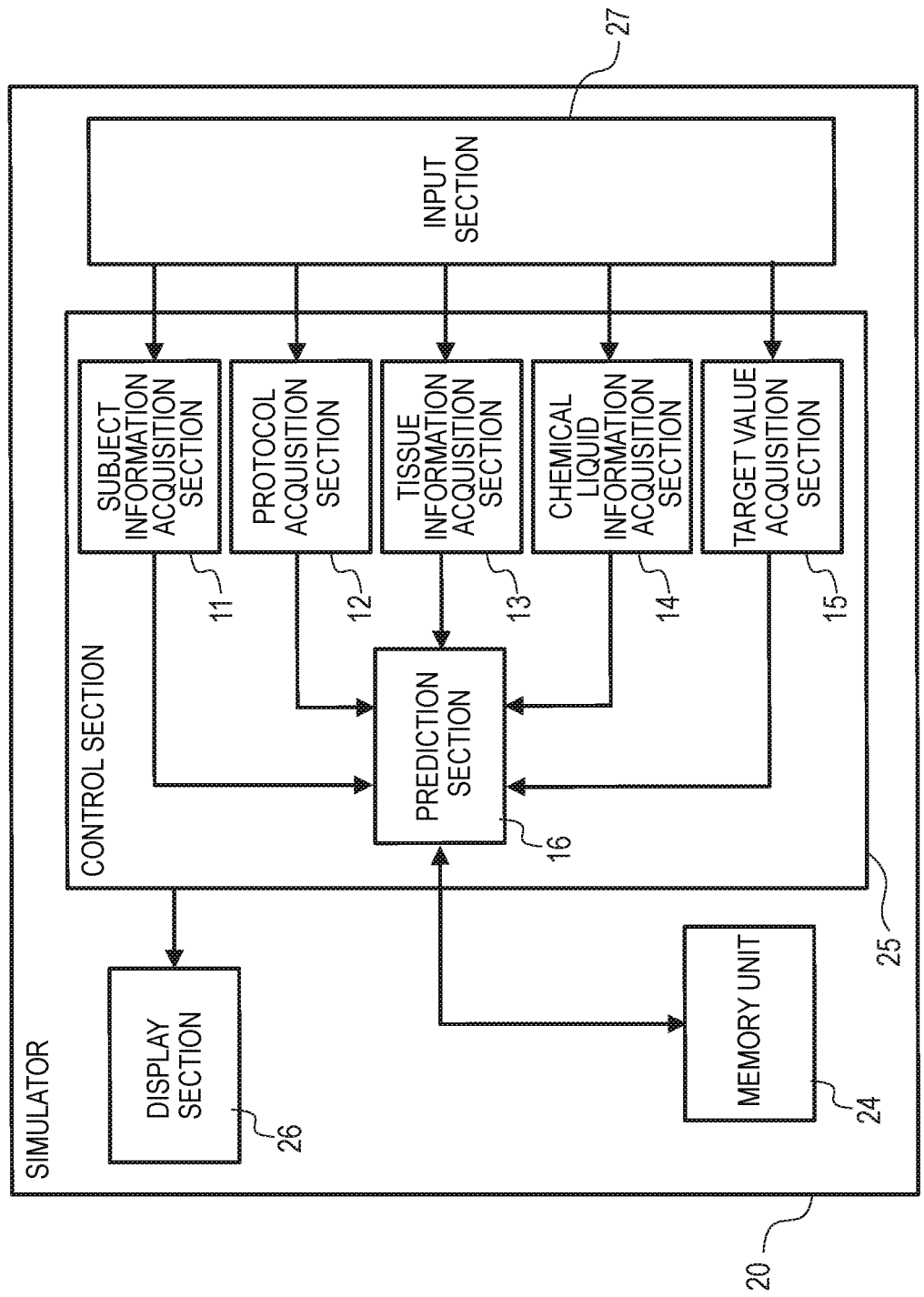
FIG. 1 is a schematic block diagram of a simulator.

A simulator (perfusion simulator) 20, which predicts a time-dependent change in the pixel value in a tissue of a subject, includes a subject information acquisition section 11, which acquires subject information on an examinee who is the subject, as shown in FIG. 1. The subject information includes, for example, a hemoglobin level, a body mass, a height, a body surface area, a cardiac function, a heart rate, a stroke volume, a cardiac output, an estimated glomerular filtration rate (eGFR), a creatinine level, an age, a gender, a fat-free body mass, a body mass index, a circulating blood volume, an examinee number (examinee ID), a history of diseases and side-effects of the examinee, the name of the examinee, the date of birth, a blood volume, and a blood flow speed.

The subject information acquisition section 11 acquires subject information inputted by a user via an input section 27 of the simulator 20. The subject information acquisition section 11 may acquire the subject information from a memory unit 24 of the simulator 20 or an external storage device (server). The server is, for example, a radiology information system (RIS), a picture archiving and communication system (PACS), a hospital information system (HIS), an image examination system, and an image creation workstation. Further, the subject information acquisition section 11 may acquire the subject information from an imaging device 3 or an injection device 2 shown in FIG. 5.

The simulator 20 includes a protocol acquisition section 12, which acquires a contrast medium injection protocol. The protocol acquisition section 12 acquires an injection protocol inputted by the user via the input section 27. The injection protocol includes a chemical liquid injection period and a chemical liquid injection speed by way of example.

The injection protocol may further include an injection method, a contrast medium injection location, an amount of injection, an injection timing, a contrast medium concentration, injection pressure, and acceleration of the injection speed. The protocol acquisition section 12 may acquire the injection protocol from the memory unit 24, the external storage device, or the injection device 2.

The injection protocol may include a contrast medium injection period and injection speed, a physiological saline injection period and injection speed, whether or not the contrast medium is injected by rear pushing, an increase or decrease in the injection speed, whether or not cross injection is performed, whether or not a speed linkage setting is made, the volume of an injection tube, and other pieces of information. The cross injection is an injection method for first injecting the contrast medium at a speed higher than the physiological saline injection speed until a set period elapses after the injection starts and then injecting not only the contrast medium in such a way that the injection speed gradually decreases but physiological saline in such a way that the injection speed gradually increases. The speed linkage setting is a setting that links the contrast medium injection speed and the physiological saline injection speed are so linked to each other that the two injection speeds are equal to each other.

The simulator 20 includes a tissue information acquisition section 13, which acquires tissue information of the subject. The tissue information includes, for example, the number of compartments in the tissue (number of divided compartments of blood vessel and organ), the volume of the tissue (volume of vascular cavity), the volume of capillaries, the volume of an extracellular sap cavity, the amount of the blood flow per unit tissue (blood flow speed), a contrast medium permeating-out speed in the tissue (capillary permeable surface area), a contrast medium permeating-back speed in the tissue (capillary permeable surface area), and a pixel value specific to the tissue. The number of compartments may be so set as to be greater in a tissue having a large volume than in a tissue having a small volume.

The tissue information acquisition section 13 acquires tissue information inputted by the user via the input section 27. The tissue includes the heart (right and left ventricles), blood vessels, kidney, ureter, and other organs and muscle. A prediction section 16, when it acquires a pixel value specific to each tissue, predicts the degree of enhancement achieved by the contrast medium based on the pixel value specific to the tissue. The tissue information acquisition section 13 may acquire the tissue information from the memory unit 24, the external storage device, or the injection device 2.

The simulator 20 includes a chemical liquid information acquisition section 14, which acquires the amount of contrast medium. The chemical liquid information acquisition section 14 further acquires chemical liquid information on a chemical liquid. The chemical liquid information acquisition section 14 acquires chemical liquid information inputted by the user via the input section 27. The chemical liquid information includes, for example, a viscosity, an osmotic pressure ratio, an amount of contrast medium, an amount of physiological saline, a product ID, a product name, a chemical liquid classification, contained components, a concentration, an expiration date, a syringe volume, a syringe withstand pressure, a cylinder inner diameter, a piston stroke, and a lot number.

The chemical liquid information acquisition section 14 may acquire the chemical liquid information from the memory unit 24, the external storage device, or the injection device 2. The chemical liquid information acquisition section 14 may further acquire the chemical liquid information from a reader built in the injection device 2. The reader reads chemical liquid information from a data carrier attached to a syringe incorporated in an injection head. The data carrier is, for example, an RFID chip, an IC tag, or a barcode.

The simulator 20 includes a target value acquisition section 15, which acquires a target duration for which a target pixel value is maintained. The user can input at least one of the target pixel value and the target duration via the input section 27.

The simulator 20 includes the prediction section 16, which simulates a time-dependent change in the pixel value in a tissue of a subject to determine a predicted duration. The prediction section 16 simulates a time-dependent change in the pixel value in the tissue of the subject based on the acquired injection protocol and the amount of the contrast medium and determines the predicted duration for which a target pixel value is maintained.

Specifically, the prediction section 16 receives as the subject information the hemoglobin level (g/dL), the body mass (kg), the height (cm), the cardiac function (%), the heart rate (bpm), the body surface area (m$^2$), the cardiac output (L/min), and the eGFR from the subject information acquisition section 11. The prediction section 16 may instead calculate at least one of the body surface area, the cardiac output, and the estimated glomerular filtration rate. For example, the body surface area can be calculated based on the body mass and the height by using the Fujimoto method, the DuBois method, or the Shinya method. The cardiac output can be calculated based on the body surface area, the cardiac function, and the heart rate. The eGFR can be calculated based on the creatinine level, the age, and the gender.

The cardiac function is so set by the user, provided that an average cardiac function is expressed by 100%, as to increase (120%, for example) when the cardiac function is superior to the average cardiac function and decrease (80%, for example) when the cardiac function is inferior to the average cardiac function. As a parameter that replaces the cardiac function, a measured cardiac output (L/min) or the ratio of a measured cardiac output to an average cardiac output may be used.

The prediction section 16 acquires, as the injection protocol, the contrast medium injection period (sec) and injection speed (mL/sec), the physiological saline injection period (sec) and injection speed (mL/sec), whether or not the cross injection is performed, and whether or not the speed linkage setting is made from the protocol acquisition section 12. Further, the prediction section 16 acquires, as the tissue information, the number of compartments in the tissue, the volume of the tissue, the volume of the capillaries, the volume of the extracellular sap cavity, the blood flow speed, two types capillary permeable surface areas, and the pixel value specific to the tissue from the tissue information acquisition section 13. The prediction section 16 acquires, as the chemical liquid information, the contrast medium concentration (mgI/mL), the osmotic pressure ratio, the viscosity (mPs.s), the amount of contrast medium (mL), and the total amount of iodine (mgI) from the chemical liquid information acquisition section 14. The prediction section 16 then calculates the amount of the iodine per body mass (kg) (mgI/kg) from the total amount of the iodine and the body mass of the subject.

The prediction section 16 can acquire examination information, such as tube voltage (kV), via the input section 27. The examination information may include an examination number (examination ID), an examination site, the date and time of the examination, the type of a chemical liquid, the name of the chemical liquid, and site information on the site to be imaged. The site information is information that allows identification of the site (range) selected as a target to be imaged. For example, the site information includes the name of an imaged site, the name of an imaging method, and the distance from a chemical liquid injection site to the imaged site. The prediction section 16 can further acquire additional information inputted by the user via the input section 27, such as an analysis period (sec). The analysis period is the length of the period for which the prediction is performed and corresponds to the X-axis (FIG. 2) length of a time-concentration curve (TDC curve).

The prediction section 16 then simulates a time-dependent change in the pixel value in the tissue of the subject in each of a plurality of compartment obtained by dividing the tissue of the subject along the blood flow direction. The simulation is performed based on the subject information, the injection protocol, and the tissue information. The prediction section 16 then associates the pixel values in each of the compartments over time with the respective tissues and stores the pixel values in the memory unit 24.

The simulator 20 includes a control section 25, which is formed, for example, of a CPU, and the memory unit 24, which stores a control program. The control section 25 controls each portion of the simulator 20 according to the control program stored in the memory unit 24. The control section 25 includes the subject information acquisition section 11, the protocol acquisition section 12, the tissue information acquisition section 13, the chemical liquid information acquisition section 14, and the target value acquisition section 15. The sections described above are logically achieved as a variety of functions when the control section 25 carries out a variety of processes in correspondence with the control program implemented in the memory unit 24. The control section 25 further functions as a display control section that controls a display section 26.

The memory unit 24 includes a RAM (random access memory) that is a system work memory for allowing the control section 25 to operate, a ROM (read only memory) that stores a program or system software, or a hard disk drive. The memory unit 24 stores a simulation program that causes a computer (control section 25) to predict a time-dependent change in the pixel value in the tissue of the subject.

The simulation program causes the computer to function as the chemical liquid information acquisition section 14, which acquires the amount of the contrast medium, the target value acquisition section 15, which acquires a target duration for which a target pixel value is maintained, the protocol acquisition section 12, which acquires the contrast medium injection protocol, and the prediction section 16, which simulates the time-dependent change based on the injection protocol and the amount of the contrast medium and determines a predicted duration. The simulation program further causes the computer to function as the prediction section 16 that compares the predicted duration with the target duration and, when the predicted duration is shorter than the target duration, re-simulates the time-dependent change in a case where a greater amount of the contrast medium is injected than the amount of the contrast medium used in the simulation to redetermine the predicted duration, whereas, when the predicted duration is longer than the target duration, re-simulating the time-dependent change in a case where a smaller amount of the contrast medium is injected than the amount of the contrast medium used in the simulation to redetermine the predicted duration. The simulation program can be stored on a computer readable recording medium.

The control section 25 can instead control the variety of processes according to the control program and the simulation program stored on a CD (compact disc), a DVD (digital versatile disc), a CF (compact flash) card, or any other portable recording medium, or a server on the Internet or any other external recording medium.

The simulator 20 includes the display section 26, which displays each of the compartments of the tissue in a color having a density according to the pixel value. The control section 25 then changes the grayscale of the compartment of the tissue displayed on the display section 26 according to a time-dependent change in the pixel value. To this end, the control section 25 reads the pixel value in the compartment at selected time from the memory unit 24 and changes the grayscale of the compartment. The display section 26 displays a main screen (FIG. 2), an automatic optimization screen (FIG. 3), and other operation screens. The display section 26 may display the injection protocol, the input state of the device, the setting state, and the result of the injection.

The simulator 20 includes the input section 27, which is connected to the subject information acquisition section 11, the protocol acquisition section 12, the tissue information acquisition section 13, and the chemical liquid information acquisition section 14. The input section 27 can, for example, be a keyboard. A touch panel that serves both as the input section 27 and the display section 26 may instead be used.

[Prediction of Time-Dependent Change in Pixel Value]

Each tissue of the subject is divided into a plurality of compartments along the blood flow direction according to the number of compartments to which the tissue is divided acquired from the tissue information acquisition section 13. The prediction section 16 predicts a time-dependent change in the pixel value in each of the compartments by dividing the volume of the tissue including the compartment under prediction, the volume of the capillaries in the tissue, and the volume of the extracellular sap cavity in the tissue by the number of divided compartments. For example, in a case where the number of divided compartments is 15, the prediction section 16 predicts a time-dependent change in the pixel value based on the quotients of the volume of the tissue, the volume of the capillaries, and the volume of the extracellular sap cavity divided by 15.

Tissues of a subject include the right ventricle, main artery, vein, artery, brain (head), upper limb, heart muscle (heart muscle in which right coronary artery is dominant, heart muscle in which anterior descending branch is dominant, heart muscle in which circumflex branch is dominant), lung, liver, stomach, spleen, pancreas, intestinal tract, kidney, ureter, lower limb, left ventricle, ascending main artery, descending main artery, and abdominal main artery. The contrast medium injected via the upper limb vein moves through the right ventricle, the lung, the left ventricle, and the main artery (ascending main artery, descending main artery) to each organ and then reaches the right ventricle via the vein. The contrast medium injected into the body is then discharged out of the body via the kidney and the ureter.

The prediction section 16 predicts a time-dependent change in the pixel value of each tissue sequentially from the right ventricle toward the upstream and downstream in the blood flow direction. For example, the prediction section 16 first performs the prediction on the right ventricle and then performs the prediction on a second tissue group including the main vein and the vein located on the upstream side of the right ventricle in the blood flow direction and the artery located on the downstream side of the right ventricle in the blood flow direction. That is, the prediction section 16 predicts a time-dependent change in the pixel value of each tissue sequentially from a tissue close to the contrast medium injection location toward tissues on the upstream and downstream in the blood flow direction.

The prediction section 16 uses a differential equation, for example, the following Equation 1 to determine a change in the pixel value in each tissue (blood vessels and organs) in the form of a time function. In Equation 1, $C_1$ represents the concentration of the contrast medium flowing into the compartment, $C_2$ represents the concentration of the contrast medium flowing out of the compartment, V represents the volume of the compartment, and Q represents the amount of blood flow per unit tissue (blood flow speed) in the compartment.

[Math. 1]

$$V \cdot \frac{dC_2}{dt} = QC_1 - QC_2 \quad \text{(Equation 1)}$$

Further, to determine a change in the pixel value in a tissue other than the right ventricle, the left ventricle, and the blood vessels, the prediction section 16 takes the following speeds into account: the permeation-out speed of the contrast medium that passes from the capillaries to the extracellular sap cavity; and the permeation-back speed of the contrast medium that passes from the extracellular sap cavity to the capillaries. The prediction section 16 therefore uses differential equations, for example, the following Equations 2 and 3. In Equations 2 and 3, Vec represents the volume of the extracellular sap cavity, Cec represents the concentration of the contrast medium in the extracellular sap cavity, Viv represents the volume of the capillaries, Civ represents the concentration of the contrast medium in the capillaries, $PS_1$ represents the permeation-out speed, and $PS_2$ represents the permeation-back speed.

[Math. 2]

$$Vec \cdot \frac{dCec}{dt} = PS_1 Civ - PS_2 Cec \quad \text{(Equation 2)}$$

[Math. 3]

$$Viv \cdot \frac{dCiv}{dt} = (QC_1 - QCiv) - (PS_1 Civ - PS_2 Cec) \quad \text{(Equation 3)}$$

Solving the differential equations described above allows the elapsed period after the injection starts and a change in the pixel value (contrast medium concentration) in the form of a time function. The parameters used for the prediction in the case of stomach are, for example, as follows: the tissue volume greater than or equal to 120 mL but smaller than or equal to 160 mL; the capillary volume greater than or equal to 2 mL but smaller than or equal to 5 mL; the extracellular sap cavity volume greater than or equal to 12 mL but smaller than or equal to 18 mL; the amount of the blood flow per unit tissue (artery blood flow speed) greater than or equal to 120 mL/min but smaller than or equal to 180 mL/min; the permeation-out speed higher than or equal to 15 but lower than or equal to 25; and the permeation-back speed higher than or equal to 15 but lower than or equal to 25.

In the case of spleen, the following parameters are used: the tissue volume greater than or equal to 120 mL but smaller than or equal to 160 mL; the capillary volume greater than or equal to 10 mL but smaller than or equal to 15 mL; the extracellular sap cavity volume greater than or equal to 45 mL but smaller than or equal to 65 mL; the amount of the blood flow per unit tissue greater than or equal to 150 mL/min but smaller than or equal to 250 mL/min; the permeation-out speed higher than or equal to 15 but lower than or equal to 25; and the permeation-back speed higher than or equal to 15 but lower than or equal to 25.

In the case of pancreas, the following parameters are used: the tissue volume greater than or equal to 120 mL but smaller than or equal to 150 mL; the capillary volume greater than or equal to 3 mL but smaller than or equal to 6 mL; the extracellular sap cavity volume greater than or equal to 30 mL but smaller than or equal to 50 mL; the amount of the blood flow per unit tissue greater than or equal to 120 mL/min but smaller than or equal to 180 mL/min; the permeation-out speed higher than or equal to 15 but lower than or equal to 25; and the permeation-back speed higher than or equal to 15 but lower than or equal to 25.

In the case of intestinal tract, the following parameters are used: the tissue volume greater than or equal to 1800 mL but smaller than or equal to 20000 mL; the capillary volume greater than or equal to 30 mL but smaller than or equal to 40 mL; the extracellular sap cavity volume greater than or equal to 500 mL but smaller than or equal to 600 mL; the amount of the blood flow per unit tissue greater than or equal to 0.4 mL/min but smaller than or equal to 0.5 mL/min; the permeation-out speed higher than or equal to 150 but lower than or equal to 250; and the permeation-back speed higher than or equal to 150 but lower than or equal to 250. The permeation-out speed and the permeation-back speed can each be calculated in the form of the product of the capillary area and the permeability. For example, assuming that the total area of the capillaries in a human body is 800 m², and a capillary area according to the mass of an organ is allocated to the organ. Assuming then that the permeability of each organ is 1 ml/min/g, and the permeation-out speed and the permeation-back speed can be calculated.

Further, the prediction section 16 takes into account the fact that the contrast medium diffuses between adjacent compartments. That is, the prediction section 16 predicts time-dependent changes in the pixel values in adjacent compartments in such a way that the concentration of the contrast medium in a high-concentration compartment is decreased but the concentration of the contrast medium in a low-concentration compartment is increased. In a case where there is a large difference in the concentration between the adjacent compartments, the prediction section 16 increases the amounts of increase and decrease in the contrast medium concentration.

In a case where the contrast medium osmotic pressure ratio is large, the prediction section 16 increases the amounts of increase and decrease in the contrast medium concentration. Further, in a case where the area where compartments are in contact each other is large, the prediction section 16 increases the amounts of increase and decrease in the contrast medium concentration. Specifically, in a case where different-tissue compartments are adjacent to each other, the prediction section 16 decreases the amounts of increase and decrease in the contrast medium concentration because the contact area decreases. In a case where same-tissue compartments are adjacent to each other, the prediction section 16 increases the amounts of increase and decrease in the contrast medium concentration because the contact area increases.

[Discharge of Contrast Medium]

Part of the contrast medium injected into an actual body does not recirculate because it is discharged out of the body via the kidney and the ureter. The prediction section 16 therefore calculates the discharged amount of the contrast medium based on a predetermined discharge speed and subtracts the discharged amount from the amount of the contrast medium in the capillaries in the kidney for the simulation. As a result, part of the contrast medium having reached the kidney is subtracted from the total amount of contrast medium in the overall body (blood plasma). Specifically, the prediction section 16 allocates the contrast medium having reached the kidney to the capillaries, the extracellular sap cavity, and the cell parenchym. The prediction section 16 then divides the contrast medium allocated to the capillaries in the kidney into three parts and allocates the three parts to the kidney artery, the extracellular sap cavity in the kidney, and the ureter. That is, the prediction section 16 moves the discharged amount of the contrast medium from the kidney capillaries to the ureter for the simulation. The contrast medium moved to the ureter does not return into the body. As a result, the contrast medium moved to the ureter is subtracted from the total amount of contrast medium in the overall body.

The contrast medium moved to the ureter increases in proportion to the concentration of the contrast medium in the kidney capillaries. That is, the contrast medium discharge speed (mL/sec) increases in proportion to the concentration of the contrast medium in the capillaries. The contrast medium concentration is the ratio of the contrast medium in the tissue (compartment) to the contrast medium in the blood on a unit time (10 msec, for example) basis. The contrast medium injected into an actual body increases in proportion to eGFR. The prediction section 16 then multiplies eGFR by an adjustment coefficient and further multiplies the contrast medium concentration by the value that is the result of the first multiplication to determine the contrast medium discharge speed. The adjustment coefficient is greater than zero but smaller than five. The total amount of the contrast medium in the overall body decreases over time as a result of the simulation of the discharge of the contrast medium, whereby the simulation can be performed with higher precision. Further, the prediction section 16 may subtract the contrast medium in the ureter after a predetermined period elapses so that the simulation reflects the fact that the contrast medium in the ureter is pushed by urine and moved into the bladder.

After the simulation is completed, the prediction section 16 causes the memory unit 24 to successively store the results of the simulation. The results of the simulation include information on the pixel value for each point of time related to a tissue. The display section 26 then diagrammatically displays a predicted image of each tissue including a plurality of compartments. Further, the control section 25 reads the pixel values from the memory unit 24 and controls the display section 26 in such a way that the grayscale of each compartment is changed according to the time-dependent change in the pixel value.

[Main Screen]

A main screen as an example of a screen displayed on the display section 26 will be described with reference to FIG. 2. The main screen is an operation screen that allows the user to input a variety of numerical values, and a predicted image 41 is disposed on the right of the main screen. A condition setting field 42 is disposed in an upper left portion of the main screen, and a time-concentration curve field 43 is disposed in a central upper portion of the main screen. Display buttons 44 are disposed in a central lower portion of the main screen, and a patient setting field 45 is disposed in a lower right portion of the main screen.

In the time-concentration curve field 43, the horizontal axis corresponds to the elapsed time (sec) after the injection starts, and the vertical axis corresponds to the pixel value (HU). It is, however, noted that in a case where the total amount of the contrast medium is displayed, the vertical axis corresponds to the amount of the contrast medium (mL). In the time-concentration curve field 43, time-concentration curves associated with a plurality of tissues can be so displayed as to be superimposed on one another. In this case, the control section 25 displays the time-concentration curves in different colors.

The user can operate a scrollbar 431 below the time-concentration curve field 43 to move a current time point bar 432 rightward and leftward in FIG. 2. The control section 25 reads from the memory unit 24 the pixel value in each compartment at the time selected by the user's operation of the scrollbar 431. The control section 25 then reflects the read pixel values in the predicted image 41 and causes the display section 26 to display the image. For example, in FIG. 2, the point of time when 31.0 seconds have elapsed since the injection started has been selected, and a predicted image 41 at the selected point of time is displayed. In an initial setting, a predicted image 41 at the injection start point of time, that is, at the point of time when 0 seconds have elapsed since the injection started is displayed.

Figure 2:
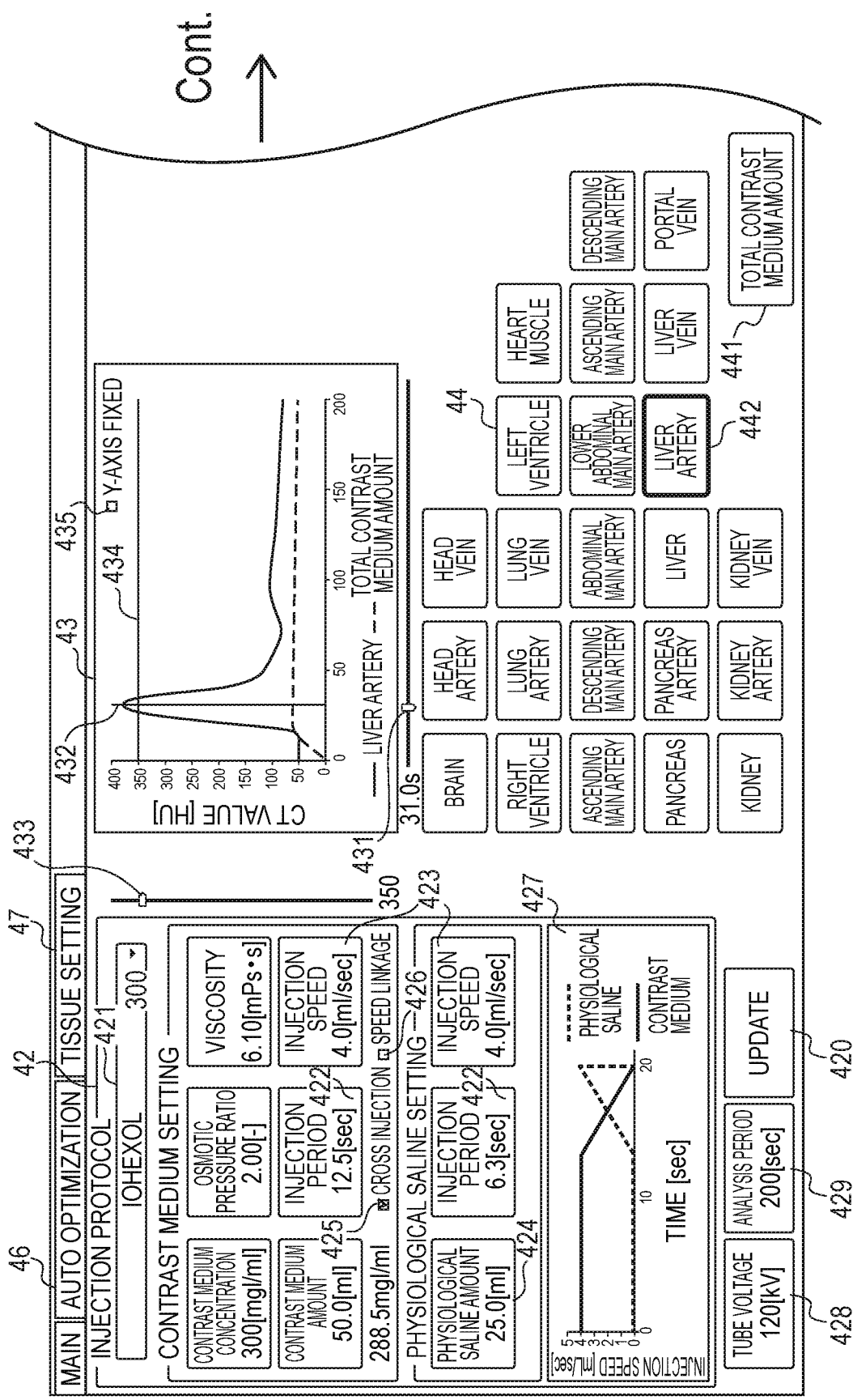
FIG. 2 is a view of a main screen displayed on a display section of the simulator.
Figure 2:
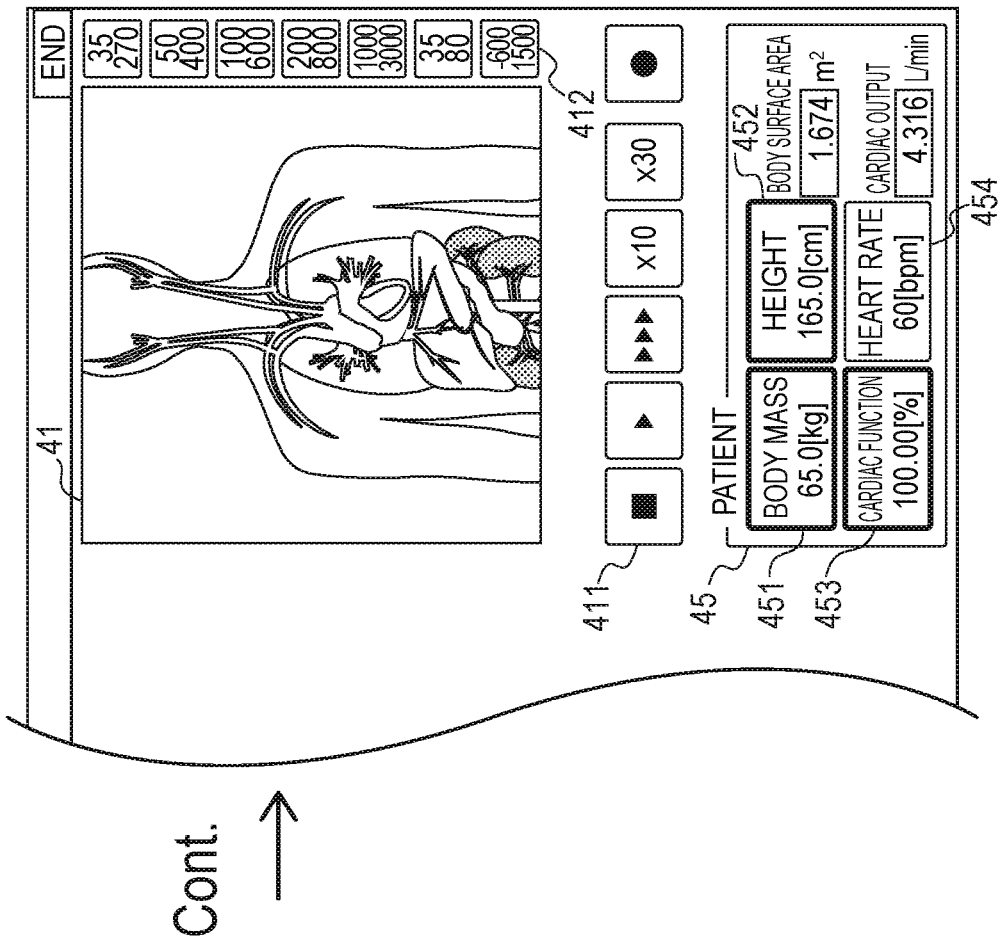

The user can operate a scrollbar 433 on the left of the time-concentration curve field 43 to move a pixel value bar 434 upward and downward in FIG. 2. The control section 25 displays, in a position below the scrollbar 433, the pixel value in the position selected by the user's operation of the scrollbar 433. For example, in FIG. 2, a pixel value 350 HU has been selected and displayed in the position below the scrollbar 433. Further, the user can select a Y-axis fixing check box 435 to fix the maximum on the Y axis (in FIG. 2, Y-axis fixing setting has not been selected). For example, in a case where the maximum on the Y axis is fixed at 400, the maximum on the Y axis is maintained at 400 even when only the total amount of the contrast medium (50.0 mL at the maximum, for example) is displayed. On the other hand, in the case where the Y-axis fixing setting has not been selected, and when only the total amount of the contrast medium of, for example, 50.0 mL at the maximum is displayed, the maximum on the Y axis is changed to 50.

The user can manipulate the image by operating operation buttons 411 below the predicted image 41. The operation buttons 411 include a stop button, a reproduction button, a triple-speed reproduction button, a 10-times-speed reproduction button, a 30-times-speed reproduction button, and a reset button sequentially from the left of the main screen. When the user selects the reproduction button, the predicted image 41 is continuously reproduced in the form of motion images over the elapsed time. When the user selects any of the triple-speed reproduction button, the 10-times-speed reproduction button, and the 30-times-speed reproduction button, the motion image reproduction speed increases. The user can therefore visually recognize the position of the contrast medium in each tissue at a desire point of time. The current time point bar 432 moves along the X axis in correspondence with the elapsed time when the predicted image 41 is continuously reproduced. When the user selects the stop button, the reproduction temporarily is suspended.

When the user selects the reset button, the reproduction is terminated, and the predicted image 41 returns to the initial setting (point of time when zero seconds have elapsed after injection started).

To select a window width (WW) and a window level (WL), a plurality of WL/WW selection buttons 412 are disposed on the right of the predicted image 41 in the main screen. The window width corresponds to the range of the contrast of the pixel value, and the window level corresponds to the brightness of the screen. In FIG. 2, a window width of 400 and a window level of 50 have been set. In a case where a pixel value is smaller than the value obtained by subtracting half the value of the window width from the value of the window level, the display section 26 displays the pixel value in black. In a case where a pixel value is greater than the value obtained by adding half the value of the window width to the value of the window level, the display section 26 displays the pixel value in white. Further, the display section 26 displays a non-contrasted tissue by using the specific pixel value. Input fields into which the window width and the window level are inputted may instead be disposed in the main screen.

A plurality of display buttons 44, which allow the user to select a tissue to be displayed, are disposed in a portion below the time-concentration curve field 43. The user can select a tissue to be displayed in the time-concentration curve field 43 from the display buttons 44. In FIG. 2, a liver artery button 442 and a total contrast medium amount button 441 have been selected. When the user selects the total contrast medium amount button 441, a change in the total amount of the contrast medium left in the body is displayed in the time-concentration curve field 43.

In the condition setting field 42, the chemical liquid information, the injection protocol, the tube voltage, and the analysis period can be set. Specifically, the user can operate a chemical liquid pulldown menu 421 to select one of a plurality of chemical liquid names. When the user selects a chemical liquid, the chemical liquid information acquisition section 14 acquires the contrast medium concentration, the viscosity, the osmotic pressure ratio, and the amount of the contrast medium corresponding to the chemical liquid name selected by the user. The contrast medium concentration, the viscosity, the osmotic pressure ratio, and the amount of the contrast medium have been inputted in advance to the memory unit 24.

The chemical liquid information acquisition section 14 can instead acquire the contrast medium concentration, the viscosity, the osmotic pressure ratio, and the amount of the contrast medium inputted by the user via the input section 27. Specifically, when the user selects the contrast medium concentration button, the control section 25 displays a contrast medium concentration input screen on the display section 26. The user can then input a desired contrast medium concentration via the input screen. Similarly, the user can input the contrast medium concentration, the viscosity, the osmotic pressure ratio, and the amount of the contrast medium. According to the input, the control section 25 displays the contrast medium concentration, the viscosity, the osmotic pressure ratio, and the amount of the contrast medium acquired by the chemical liquid information acquisition section 14 in a contrast medium display field.

In a contrast medium setting field, the user can select an injection period button 422 to input a contrast medium injection period in the injection protocol. When the user selects the injection period button 422, the control section 25 displays an injection period input screen on the display section 26. The user can then input a desired injection period via the input screen. Similarly, the user can select an injection speed button 423 to input a contrast medium injection speed in the injection protocol. Further, a per-body-mass contrast medium amount button may be disposed in the contrast medium setting field so that a contrast medium amount per body mass (mgI/kg) can be inputted. In this case, when the contrast medium amount per body mass is inputted, the prediction section 16 multiplies the amount of the contrast medium per body mass by the body mass to automatically change the amount of the contrast medium.

The user can select a cross injection check box 425 to select whether or not the cross injection is performed. In FIG. 2, the selection has been so made that the cross injection is performed. Similarly, the user can select a speed linkage setting check box 426 to select whether or not the speed linkage setting is made. In FIG. 2, the speed linkage setting has not been selected.

In a physiological saline setting field, the user can select an injection period button 422 to input a physiological saline injection period in the injection protocol. When the user selects the injection period button 422, the control section 25 displays an injection period input screen on the display section 26. The user can then input a desired injection period via the input screen. Similarly, the user can select an injection speed button 423 and a physiological saline amount button 424 to input a physiological saline injection speed and a physiological saline amount in the injection protocol, respectively.

An injection amount display screen 427 is disposed in a portion below the physiological saline setting field. In the injection amount display screen 427, the horizontal axis represents the elapsed time after the injection starts, and the vertical axis represents the injection speed. In the injection amount display screen 427, the control section 25 displays the injection amount in the injection protocol acquired by the protocol acquisition section 12. In FIG. 2, the setting has been so made that the cross injection is performed, and the injection amount display screen 427 displays a graph showing that the contrast medium is injected at an injection speed of 4.0 mL/sec and the injection speed gradually decreases after a predetermined period elapses. The graph is so drawn that the area of the region surrounded by the solid line represents the amount of the injected contrast medium. In this case, the prediction section 16 predicts a time-dependent change in the pixel value in each tissue with the cross injection reflected.

Further, in the injection amount display screen 427, a graph representing the injection of the physiological saline is so displayed as to show that after the contrast medium injection starts and a predetermined period then elapses, injection of physiological saline starts, and the injection speed of the physiological saline gradually increases and reaches the injection speed of 4.0 mL/sec after a predetermined period elapses. The graph is so drawn that the area of the region surrounded by the dotted line represents the amount of the injected physiological saline. The region representing the amount of the injected contrast medium and the region representing the amount of the injected physiological saline may be so displayed as to be filled with different colors.

In a case where the selection has been so made that no cross injection is performed, the graph is so displayed as to show that the injection of the physiological saline starts after the injection of the contrast medium is completed. For example, the graph is so displayed as to show that the contrast medium is injected at the injection speed of 4.0 mL/sec after the injection starts, the physiological saline is injected at the injection speed of 4.0 mL/sec when the injection of the contrast medium of 50.0 mL is completed, and the injection is terminated when the injection of the physiological saline of 25.0 mL is completed.

In a case where the speed linkage setting has been selected, the contrast medium injection speed and the physiological saline injection speed are so set as to be equal to each other. For example, in a case where the contrast medium injection speed is changed from 4.0 mL/sec to 5.0 mL/sec, the physiological saline injection speed is automatically set at 5.0 mL/sec. In this case, input of a physiological saline injection speed may be prohibited. Further, in a case where the physiological saline injection speed is changed, the contrast medium injection speed may be automatically set.

A tube voltage button 428, an analysis period button 429, and an update button 420 are disposed in a portion below the injection amount display screen 427. The user can select the tube voltage button 428 to set the tube voltage. When the user selects the tube voltage button 428, the control section 25 displays a tube voltage input screen on the display section 26. The user can then input desired tube voltage via the input screen. Similarly, the user can select the analysis period button 429 to input an analysis period.

The patient setting field 45 is disposed in a portion below the operation buttons 411. In the patient setting field 45, the body mass, height, cardiac function, and heart rate can be set. The control section 25 displays in advance the body mass, height, cardiac function, and heart rate in the patient setting field 45 based on the subject information acquired by the subject information acquisition section 11. The subject information acquisition section 11 can also acquire a body mass, height, cardiac function, and heart rate inputted by the user via the input section 27. Specifically, when the user selects a body mass button 451, the control section 25 displays a body mass input screen on the display section 26. The user can then input a body mass of the subject via the input screen. Similarly, the user can select a height button 452, a cardiac function button 453, and a heart rate button 454 to input a height, cardiac function, and heart rate of the subject, respectively.

A body surface area field and a cardiac output field are disposed in the patient setting field 45. The prediction section 16 calculates the body surface area based on the body mass and height of the subject acquired by the subject information acquisition section 11. The control section 25 displays the calculated body surface area in the body surface area field. When the user inputs a body mass or any other parameter of the subject, the subject information acquisition section 11 acquires the inputted body mass or any other parameter. Similarly, the prediction section 16 calculates the cardiac output based on the body surface area, the cardiac function, and the heart rate of the subject acquired by the subject information acquisition section 11. The control section 25 displays the calculated cardiac output in the cardiac output field.

An eGFR field, a creatinine level button, an age button, and a gender button may further be disposed in the patient setting field 45. In this case, the user can select the creatinine level button, the age button, and the gender button to input a creatinine level, age, and gender of the subject, respectively. The subject information acquisition section 11 acquires the inputted creatinine level and the like. The prediction section 16 calculates eGFR based on the acquired creatinine level, age, and gender of the subject. The control section 25 displays the calculated eGFR in the eGFR field. Instead, the subject information acquisition section 11 can also acquire the heart rate from an external measurement tool or the memory unit 24. Further, the subject information acquisition section 11 can also acquire the stroke volume or the cardiac output from an external measurement tool. In the case where the stroke volume is acquired, the prediction section 16 multiplies the stroke volume by the heart rate to calculate the cardiac output.

Upon completion of the setting, the user selects the update button 420. A variety of pieces of inputted information are thus acquired. The prediction section 16 then performs the simulation according to the variety of pieces of acquired information and causes the memory unit 24 to store the result of the simulation. The control section 25 then reads the result of the simulation from the memory unit 24 and displays a predicted image 41 of a tissue corresponding to the display button 44 selected by the user. Similarly, the control section 25 displays a time-concentration curve associated with the tissue corresponding to the display button 44 selected by the user in the time-concentration curve field 43.

An automatic optimization tab 46 and a tissue setting tab 47 are disposed on the right of a main screen tub in FIG. 2. When the user selects the automatic optimization tab 46, the control section 25 displays an automatic optimization screen (FIG. 3) on the display section 26. The user can then automatically optimize the injection protocol via the automatic optimization screen. When the user selects the tissue setting tab 47, the control section 25 displays a tissue setting screen (not shown) on the display section 26. The user can then input tissue information (for example, volume of tissue, volume of capillaries, volume of extracellular sap cavity, an amount of blood flow per unit tissue, permeation-out speed of contrast medium in tissue, and permeation-back speed of contrast medium in tissue) via the tissue setting screen.

[Automatic Optimization Screen]

Figure 3:
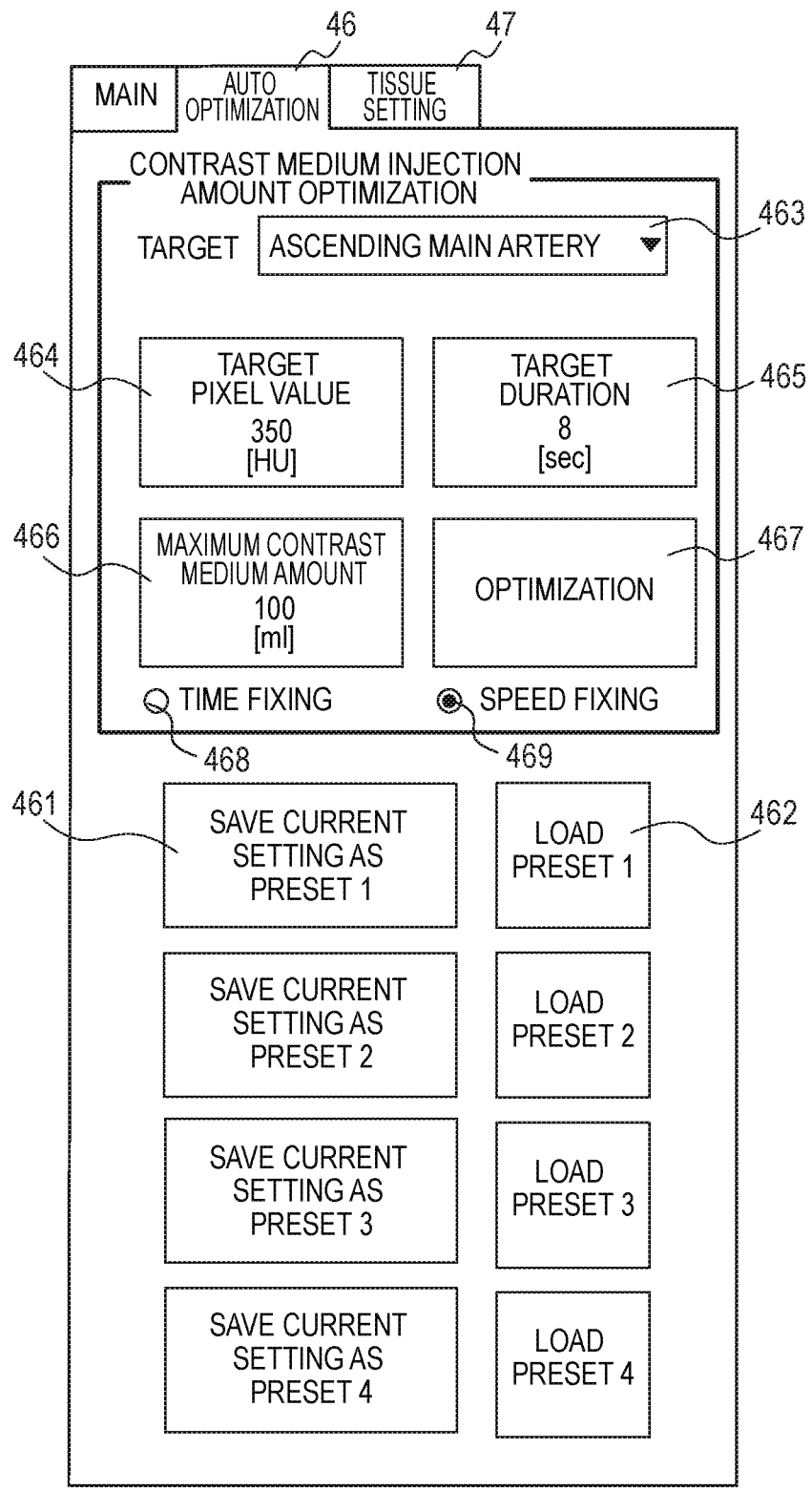
FIG. 3 a view of an automatic optimization screen displayed on the display section of the simulator.

FIG. 3 shows the automatic optimization screen for automatic optimization of the injection protocol. An optimization setting field is disposed in an upper portion of the automatic optimization screen, and preset buttons 461 and load buttons 462 are disposed in a lower portion of the automatic optimization screen. When the user selects an optimization button 467 in the automatic optimization screen, the prediction section 16 automatically optimizes the injection protocol.

A target pulldown menu 463, a target pixel value button 464, a target duration button 465, a maximum contrast medium amount button 466, an optimization button 467, a time fixing check box 468, and a speed fixing check box 469 are disposed in the optimization setting field. The user can operate the target pulldown menu 463 to select one of a plurality of tissues. When the user selects a target tissue, the tissue information acquisition section 13 acquires tissue information corresponding to the target tissue selected by the user.

The user can select the target pixel value button 464 to input a target pixel value. When the user selects the target pixel value button 464, the control section 25 displays a target pixel value input screen on the display section 26. The user can then input a desired target pixel value via the input screen. Similarly, the user can select the target duration button 465 and the maximum contrast medium amount button 466 to input the target duration and a maximum amount of contrast medium, respectively.

The target value acquisition section 15 acquires the inputted target pixel value and the target duration. The chemical liquid information acquisition section 14 acquires the inputted maximum contrast medium amount. The chemical liquid information acquisition section 14 may instead acquire the amount of the contrast medium filled in the syringe as the maximum contrast medium amount based on the chemical liquid name selected by the user. The chemical liquid information acquisition section 14 may restricts the maximum contrast medium amount in such a way that the ratio between the amount of single administered contrast medium (gI) and eGFR is smaller than one. The chemical liquid information acquisition section 14 may further refer to a table that relates eGFR and the maximum contrast medium amount to each other to acquire the maximum contrast medium amount. The table is stored in the memory unit 24 in advance.

The user can further select the time fixing check box 468 or the speed fixing check box 469 to select a time fixing or speed fixing condition. In FIG. 3, the speed fixing condition has been selected. When the speed fixing condition is selected, the prediction section 16 performs the re-simulation with no change in the injection speed. When the time fixing condition is selected, the prediction section 16 performs the re-simulation with no change in the injection period.

The user can select any of the preset buttons 461 to save the setting inputted into the optimization setting field at the time of the button selection as any of presets 1 to 4. When any of the preset buttons 461 is selected, the prediction section 16 causes the memory unit 24 to store the setting inputted as any of the presets 1 to 4 according to the selected button. The user can select any of the load buttons 462 to read the setting saved as the corresponding one of the presets 1 to 4. When any of the load buttons 462 is selected, the prediction section 16 reads any of the setting stored as the corresponding one of the presets 1 to 4 from the memory unit 24 according to the selected button. The prediction section 16 then reflects the read setting in the target pixel value and the like.

[Automatic Optimization]

Figure 4:
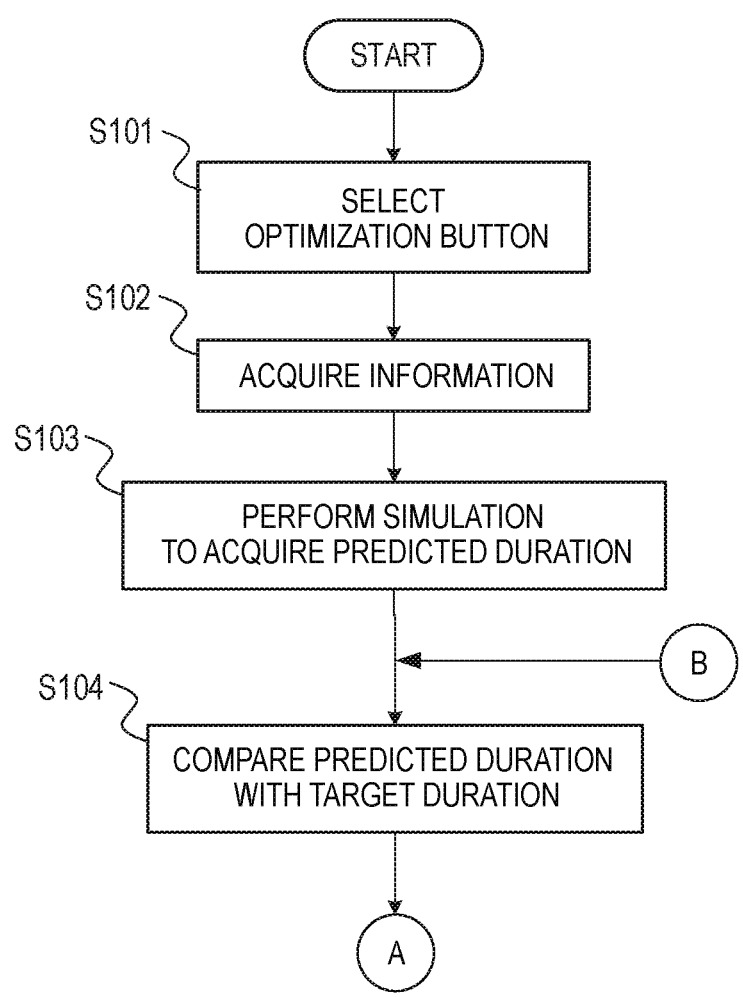
FIG. 4 is a flowchart of automatic optimization.
Figure 4:
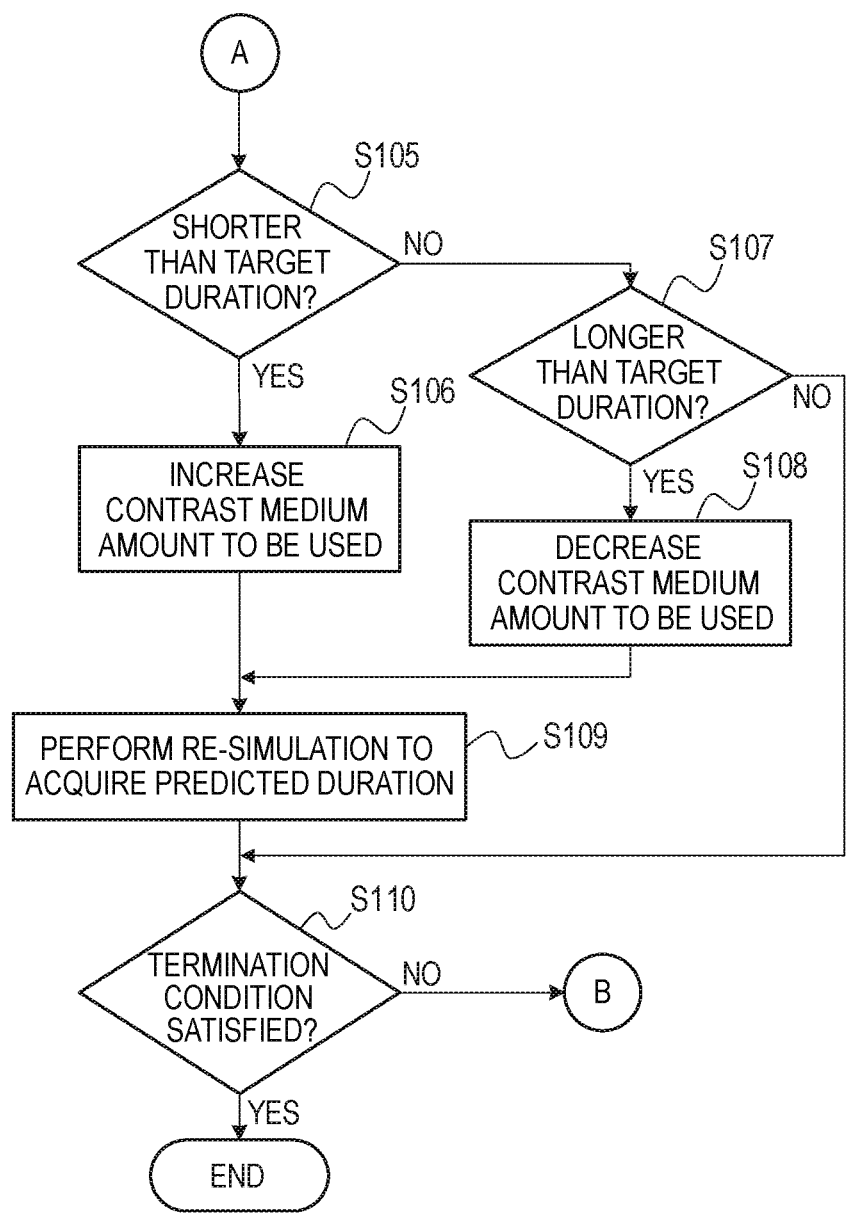

The optimization will be described below with reference to the flowchart shown in FIG. 4. When the user selects the optimization button 467 (S101), the prediction section 16 acquires a variety of pieces of information (S102), as shown in FIG. 4. Specifically, the prediction section 16 acquires a contrast medium injection protocol from the protocol acquisition section 12. The prediction section 16 further acquires a maximum contrast medium amount from the chemical liquid information acquisition section 14 and acquires a target pixel value and a target duration from the target value acquisition section 15. The prediction section 16 then simulates a time-dependent change in the pixel value in a tissue of a subject based on the acquired maximum contrast medium amount in a case where half the maximum contrast medium amount is injected as the contrast medium amount to be used according to the acquired injection protocol. The prediction section 16 then determines a predicted duration from the result of the simulation (S103).

The prediction section 16 then compares the determined predicted duration with the target duration (S104). In a case where the predicted duration is shorter than the target duration (YES in S105), the prediction section 16 re-simulates a time-dependent change in the pixel value in the tissue of the subject in a case where a greater amount of contrast medium than the amount of the contrast medium used in the preceding simulation is injected. That is, the prediction section 16 increases the amount of contrast medium to be used (S106). Specifically, a contrast medium amount $V_{n+1}$ to be used in the re-simulation is calculated by using the following Equation 4, where $V_n$ represents the amount of the contrast medium used in the preceding simulation, $T_G$ represents the target duration, and $T_A$ represents the predicted duration obtained in the preceding simulation. A weighting coefficient W in Equation 4 is, for example, 0.5. The weighting coefficient W can be lowered according to the number of repetitions of the re-simulation.

[Math. 4]

$$V_{n+1} = V_n + W(T_G - T_A) \quad \text{(Equation 4)}$$

For example, assuming that the contrast medium amount $V_n$ used in the preceding simulation is 50 mL, the target duration $T_G$ is 8 seconds, the predicted duration $T_A$ is 7.5 seconds, and the weighting coefficient W is 0.5, a contrast medium amount to be used in the re-simulation is calculated to be 50.25 mL, as shown by the following Equation 5:

[Math. 5]

$$50.25 = 50 + 0.5(8 - 7.5) \quad \text{(Equation 5)}$$

The prediction section 16 changes at least one of the contrast medium injection speed and injection period to perform the re-simulation. That is, since the amount of the contrast medium to be used increases, the prediction section 16 changes at least one of the injection speed and the injection period in the injection protocol. Specifically, in the case where the speed fixing condition is selected, the prediction section 16 does not change the injection speed but prolongs the injection period in the injection protocol. The injection period therefore is prolonged, resulting in an increase in the amount of the contrast medium to be used. In the case where the time fixing condition is selected, the prediction section 16 does not change the injection period but increases the injection speed in the injection protocol. The injection speed per unit time therefore increases, resulting in an increase in the amount of the contrast medium to be used.

In a case where the predicted duration is longer than the target duration (YES in S107), the prediction section 16 re-simulates a time-dependent change in the pixel value in the tissue of the subject in a case where a smaller amount of contrast medium than the amount of the contrast medium used in the preceding simulation is injected. That is, the prediction section 16 decreases the amount of the contrast medium to be used (S108). For example, assuming that the amount of the contrast medium $V_n$ used in the preceding simulation is 50 mL, the target duration $T_G$ is 8 sec, the predicted duration $T_A$ is 8.5 sec, and the weighting coefficient W is 0.5, an amount of the contrast medium to be used in the re-simulation is calculated to be 49.75 mL, as shown by the following Equation 6:

[Math. 6]

$$49.75 = 50 + 0.5(8 - 8.5) \quad \text{(Equation 6)}$$

Similarly, the prediction section 16 changes at least one of the contrast medium injection speed and injection period to perform the re-simulation. That is, since the amount of the contrast medium to be used decreases, the prediction section 16 changes at least one of the injection speed and the injection period in the injection protocol. Specifically, in the case where the speed fixing condition is selected, the prediction section 16 does not change the injection speed but shortens the injection period in the injection protocol. The injection period therefore shortens, resulting in a decrease in the amount of the contrast medium to be used. In the case where the time fixing condition is selected, the prediction section 16 does not change the injection period but decreases the injection speed in the injection protocol. The injection speed per unit time therefore decreases, resulting in a decrease in the amount of the contrast medium to be used.

The prediction section 16 performs the re-simulation of a time-dependent change in the pixel value in the tissue of the subject in a case where the amount of the contrast medium to be used that has been calculated according to the changed injection protocol is injected (S109). The prediction section 16 then redetermines a predicted duration from the result of the re-simulation. The prediction section 16 then causes the memory unit 24 to store the result of the re-simulation and the injection protocol used in the re-simulation. In a case where a termination condition is satisfied (YES in S110), the re-simulation is terminated. The termination condition is a case where the predicted duration coincides with the target duration, a case where the re-simulation has been performed by a predetermined number (40 times, for example), a case where a predetermined period (10 seconds, for example) has elapsed since the re-simulation started, or a case where the amount of change is smaller than or equal to a predetermined threshold. The condition that the amount of change is smaller than or equal to a predetermined threshold is a condition that the difference between the predicted duration in the current re-simulation and the predicted duration in the preceding re-simulation is smaller than or equal to a predetermined threshold (0.01 seconds, for example).

In a case where the termination condition is not satisfied (NO in S110), the prediction section 16 compares again the determined predicted duration with the target duration (S104). In the case where the predicted duration is shorter than the target duration, the prediction section 16 re-simulates a time-dependent change in the pixel value in the tissue of the subject in a case where a larger amount of contrast medium is injected. In the case where the predicted duration is longer than the target duration, the prediction section 16 re-simulates a time-dependent change in the pixel value in the tissue of the subject in a case where a smaller amount of contrast medium is injected. The prediction section 16 then redetermines the predicted duration from the result of the re-simulation.

When the re-simulation is completed, the prediction section 16 causes the memory unit 24 to store as an optimum injection protocol an injection protocol corresponding to a simulation result showing the smallest difference between the target duration and the predicted duration out of the stored re-simulation results. The prediction section 16 may instead cause the memory unit 24 to store as the optimum injection protocol an injection protocol corresponding to a simulation result showing that the predicted duration is longer than or equal to the target duration and the amount of the contrast medium to be used is the smallest out of the stored re-simulation results.

The control section 25 subsequently closes the automatic optimization screen and opens the main screen. The prediction section 16 reflects at the same time the optimum injection protocol conditions (contrast medium amount, contrast medium injection period and injection speed, physiological saline amount, and physiological saline injection period and injection speed) in the contrast medium setting field. The control section 25 then displays the optimum injection protocol in place of the injection protocol before the optimization. The control section 25 further reads a time-concentration curve based on the simulation result corresponding to the optimum injection protocol and displays the read time-concentration curve in the time-concentration curve field 43. Similarly, the control section 25 reads and displays a predicted image 41 and terminates the automatic optimization.

In a case where a result of the re-simulation shows that the target pixel value or the target duration has not been reached, the control section 25 displays a simulation condition correction proposal. That is, in a case where the target has not been achieved when the re-simulation is completed, the control section 25 displays a simulation condition correction proposal on the display section 26. The correction proposal proposes to the user by way of example a decrease in the tube voltage, an increase in the contrast medium amount (increase in contrast medium amount by 50%, for example), an increase in the injection speed (increase in injection speed by 50%, for example), or extension of the analysis period.

The invention according to the first embodiment described above allows a simulation of a time-dependent change in the pixel value in a tissue of a subject in a case where an injection protocol that maintains a target pixel value over a target duration is used. Further, the simulator 20 according to the first embodiment can perform higher-precision prediction that approximates to a time-dependent change in the pixel value in an actual tissue. Further, an optimum injection protocol that maintains a target pixel value over a target duration can be obtained.

A helical scan box may further be disposed in the main screen. The user can select the helical scan box to input a bed movement speed (cm/sec). When the helical scan box is selected, the control section 25 acquires a delay period due to the helical scan. The delay period corresponds to an elapsed period from the time when the head is imaged to the time when each tissue is imaged (bed movement period) and is determined based on the length from the upper end of the predicted image 41 to each tissue.

The control section 25 then reads the pixel value at the time which is selected by the user (current point of time) plus the delay period from the memory unit 24. That is, the control section 25 reads the pixel value in each tissue at the time obtained by adding the acquired delay period to the current point of time. A predicted image 41 for when the helical scan is performed can thus be produced. For example, in a case where the current point of time is immediately after the injection starts (0 seconds), the control section 25 shows the pixel value in the brain immediately after the injection starts and the pixel value in the right ventricle 5 seconds after the injection starts. Further, the control section 25 shows the pixel value in the liver 7.5 seconds after the injection starts.

Second Embodiment

An imaging system 100 including the simulator 20 (FIG. 1) will be described with reference to FIG. 5, which is a schematic view of an injection device and an imaging system. In the second embodiment, the simulator 20 is incorporated in at least one of the imaging system 100 and the injection device 2. The second embodiment will be described about points different from those in the first embodiment, and the components described in the first embodiment will not be described. Unless otherwise particularly described, a component having the same reference character has roughly the same action and function, and an advantageous effect provided by the component is roughly the same.

Figure 5:
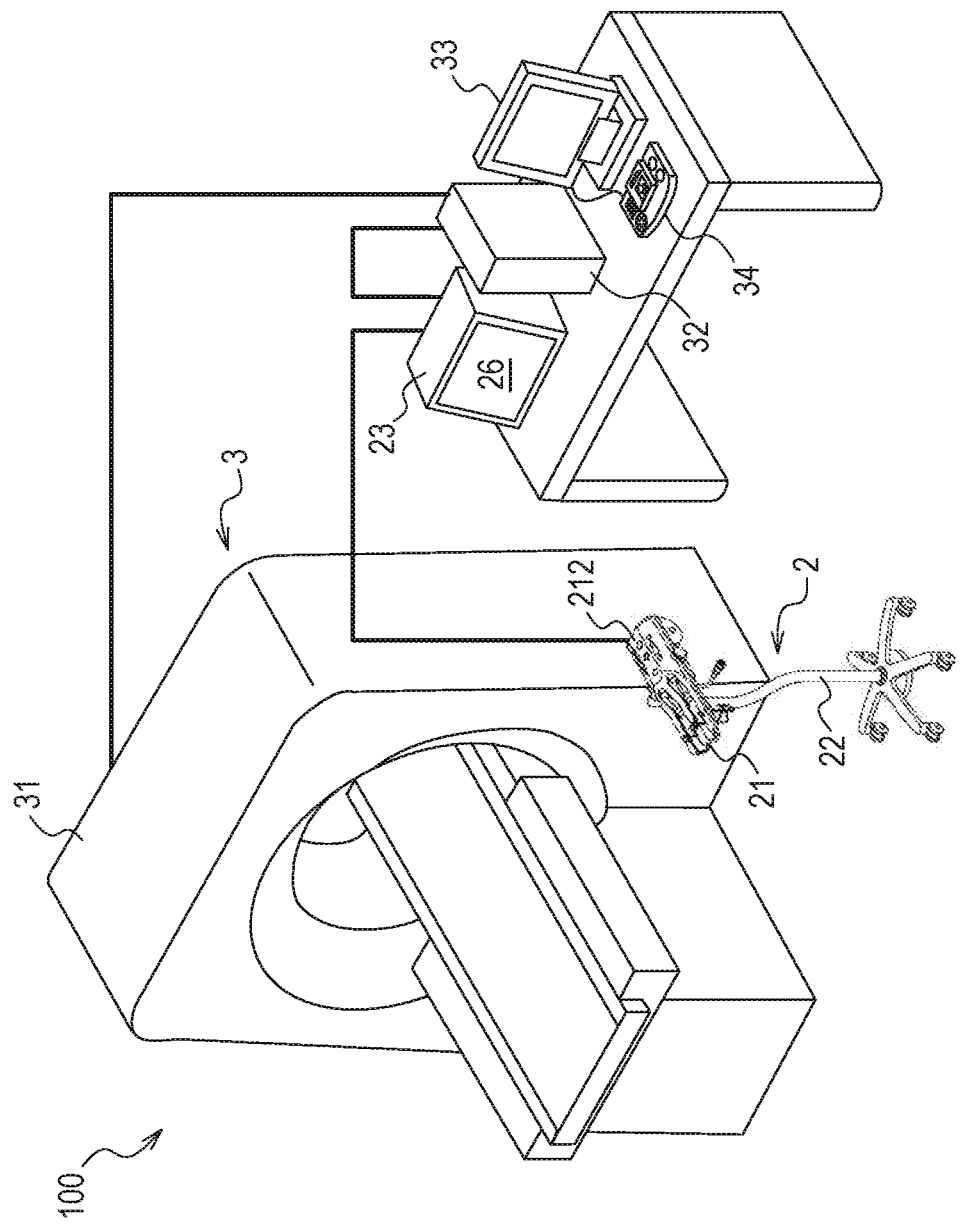
FIG. 5 is a schematic view of an injection device and an imaging system.

The imaging system 100 includes the injection device 2, which injects a contrast medium, and a medical imaging device 3, which is connected to the injection device 2 via a wire or wirelessly and captures an image of a subject, as shown in FIG. 5. The imaging device 3 is, for example, a magnetic resonance imaging (MRI) device, a computed tomography (CT) device, an angiographic imaging device, a positron emission tomography (PET) device, a single photon emission computed tomography (SPECT) device, a CT angiographic device, an MR angiographic device, an ultrasonic diagnosis device, and a blood vessel imaging device, or any of a variety of other medical imaging device. The following description will be made with reference to a CT device.

The imaging device 3 includes an imaging section 31, which captures an image of the subject according to an imaging plan, and a control device 32, which controls the entire imaging device 3. The imaging plan includes, for example, a site to be imaged, an effective tube voltage, a model name, a manufacturer name, an imaging period, tube voltage, an imaging range, a rotational speed, a helical pitch, an exposure period, a dose, and an imaging method. The control device 32 controls the imaging section 31 according to the imaging plan to cause the imaging section 31 to capture an image of the subject. The control device 32 also functions as the simulator 20. The control device 32 can communicate with the imaging section 31, the injection device 2, and a server (external storage device) via a wire or wirelessly.

The imaging section 31 includes a bed, an X-ray source that irradiates the subject with X-rays, and an X-ray detector that detects the X-rays having passed through the subject. The imaging section 31 captures a see-through image of the subject by exposing the subject to the X-rays and performing inverse projection of the interior of the subject based on the X-rays having passed through the subject. The imaging section 31 may instead perform the imaging by using a radio wave or an ultrasonic wave.

The imaging device 3 includes a display 33 as a display section. The display 33 is connected to the control device 32 and displays the input state and setting state of the imaging device 3, the result of the imaging performed by the imaging device 3, and a variety of other pieces of information. The control device 32 and the display 33 can instead be integrated with each other. Further, the imaging device 3 includes a user interface, such as a keyboard, as an input section 34. The user can input chemical liquid information, an injection protocol, tissue information, subject information, and a target value via the input section 34 to the imaging device 3.

The injection device 2 includes an injection head 21, which injects a contrast medium according to the injection protocol. The injection device 2 injects a chemical liquid with which the syringe is filled, for example, physiological saline and a variety of contrast mediums into the subject. The injection device 2 further includes a stand 22, which holds the injection head 21, and a console 23, which is connected to the injection head 21 via a wire or wirelessly.

The console 23 functions as a control device that controls the injection head 21 and also functions as the simulator 20. The console 23 includes a touch panel 26, which functions as an input display section and can communicate with the injection head 21 and the imaging device 3 via a wire or wirelessly. The touch panel 26 can display the injection protocol, the input state and setting state of the injection device, the result of the injection, and a variety of other pieces of information. The injection device 2 may include a display as the display section and a keyboard as the input section in place of the touch panel 26.

The injection device 2 may include a control device connected to the injection head 21 and a display section (touch panel display, for example) that is connected to the control device and displays a chemical liquid injection situation in place of the console 23. The control device also functions as the simulator 20. The injection head 21 and the control device can be integrated with the stand 22. Further, a ceiling hanging member can be provided in place of the stand 22, and the injection head 21 can be hung from the ceiling via the ceiling hanging member.

The injection device 2 may include a remote operation device (hand switch or footswitch, for example) that remotely operates the injection head 21. The remote operation device can remotely operate the injection head 21 to start or stop the injection. Further, the injection device 2 may include a power source or a battery. The power source or the battery can be provided in the injection head 21 or the control device or may be provided separately therefrom.

The injection head 21 includes a syringe holder on which the syringe filled with the chemical liquid is mounted and a drive mechanism that pushes the chemical liquid in the syringe according to the injection protocol. The injection head 21 includes an operation section 212, via which the action of the drive mechanism is inputted. The operation section 212 is provided, for example, with a forward button that causes the drive mechanism to produce forward motion, a backward button that causes the drive mechanism to produce backward motion, and a final check button. The injection head 21 may further include a head display that displays the injection conditions, the injection status, the input and setting states of the injection device, and a variety of injection results.

To inject the contrast medium, an extension tube or any other attachment is connected to a front-end portion of the syringe incorporated in the injection head 21. When the injection preparation is completed, the user presses the final check button on the operation section 212. The injection head 21 then waits in a state in which it is ready for injection. When the injection starts, the contrast medium pushed out of the syringe is injected through the extension tube into the body of the subject.

The syringe incorporated in the injection head 21 may include a pre-filled syringe having a data carrier, such as an RFID chip, an IC tag, and a barcode, and a variety of other syringes. The injection head 21 includes a reader (not shown) that reads the data carrier attached to the syringe. The data carrier stores chemical liquid information on the chemical liquid. Further, the injection head 21 may include at least three syringe holders or only one syringe holder.

The injection device 2 can receive information from a server (external storage device) that is not shown and transmit information to the server. The imaging device 3 can also receive information from the server and transmit information to the server. The server is, for example, an RIS (radiology information system), a PACS (picture archiving and communication system), or an HIS (hospital information system).

The server stores an examination order in advance. The examination order includes subject information on the subject and examination information on the contents of the examination. The server can store information on the result of the imaging, such as image data transmitted from the imaging device 3, and information on the result of the injection transmitted from the injection device 2. To operate the injection device 2 and the imaging device 3, an external image examination system or an image creation workstation can also be used.

In the case of the imaging device 3 according to the second embodiment, the user can operate the imaging device 3 while checking the predicted image 41 on the display 33. The imaging device 3 can change the imaging plan according to the result of the prediction performed by the prediction section 16. Specifically, the imaging device 3 can change, for example, the tube voltage or the tube current in such a way that a result of the simulation shows that a target pixel value or a target duration is reached.

Further, in the case of the injection device 2 according to the second embodiment, the user can operate the injection device 2 while checking the predicted image 41 on the console 23. The injection device 2 can change, for example, the injection speed or the injection period in such a way that the injection protocol coincides with an optimum injection protocol obtained by the automatic optimization.

The present invention has been described above with reference to the embodiments, but the present invention is not limited to the embodiments described above. An invention changed to the extent that the invention does not depart from the present invention and an invention equivalent to the present invention also fall within the scope of the present invention. Further, the embodiments and variations can be combined with each other as appropriate to the extent that the combination does not depart from the present invention.

For example, the simulator 20 may be incorporated in an external computer connected to at least one of the imaging device 3 and the injection device 2 via a wire or wirelessly. In this case, the simulator 20 transmits the result of the simulation and an optimum injection protocol to the imaging device 3 and the injection device 2, respectively.

The display section 26 can also display a coronary cross-sectional predicted image 41 as well as a horizontal cross-section of the body. Further, the display section 26 may place compartments in such a way that each tissue is displayed independently and display each of the compartments in a color having a density according to the pixel value. Further, the display section 26 may display each of the compartments in a color other than black and white.

The control section 25 may control the display section 26 in such a way that the number of compartments varies on a tissue basis. In this case, the control section 25 displays each tissue including the number of compartments set by the user or the number of compartments stored in the memory unit 24 in advance. Further, the control section 25 may display a target pixel value and a predicted duration in the time-concentration curve field 43.

The prediction section 16 may take into account a change in the amount of blood flow per unit tissue (blood flow speed) due to injection of a chemical liquid. That is, in a case where the chemical liquid injection speed is faster than a typical blood flow speed, the prediction section 16 can subtract the blood flow speed from the injection speed to produce a difference, add the difference to the blood flow speed, and take an increase in the blood flow speed into account. In this case, the prediction section 16 predicts a time-dependent change in the pixel value based on the blood flow speed to which the difference is added. That is, the prediction section 16, when it predicts a time-dependent change in the pixel value, adds the obtained difference to a blood flow speed Q per unit tissue in a compartment.

A part or the entirety of the embodiments described above can be described in the form of the following additional remarks, without being limited thereto.

(Additional remark 1) A simulator including a prediction section that repeats a re-simulation by a predetermined number or for a predetermined period.

(Additional remark 2) A simulator including a prediction section that repeats a re-simulation until a predicted duration is longer than or equal to a target duration.

This application claims the benefit of Japanese Patent Application No. 2017-130873, filed Jul. 4, 2017, which is hereby incorporated by reference herein in its entirety.

What is claimed is:

1. A simulator comprising:
a central processing unit (CPU) configured to acquire an amount of contrast medium;
the CPU configured to acquire a target duration which is to be previously set for a target pixel value of a tissue of a subject;
the CPU configured to acquire a contrast medium injection protocol; and
the CPU configured to simulate a time-dependent change in a pixel value in the tissue of the subject based on the injection protocol and the amount of the contrast medium to determine a predicted duration from when the pixel value reaches the target pixel value until the pixel value is not greater than or equal to the target pixel value, wherein
the CPU compares the predicted duration with the target duration in a simulation procedure, in a case where the predicted duration is shorter than the target duration, calculates an increase amount by multiplying a difference of the target duration and the predicted duration with a weighting coefficient and re-simulates the time-dependent change in a condition where a first amount of the contrast medium, which is obtained by adding the increase amount to a used amount of the contrast medium used in the simulation, is injected to redetermine the predicted duration, and in a case where the predicted duration is longer than the target duration, calculates a decrease amount by multiplying the difference of the target duration and the predicted duration with the weighting coefficient and re-simulates the time-dependent change in a condition where a second amount of the contrast medium, which is obtained by subtracting the decrease amount from the used amount of the contrast medium, is injected to redetermine the predicted duration.

2. A simulator according to claim 1, wherein the re-simulation is performed by changing at least one of a contrast medium injection speed and a contrast medium injection period.

3. A simulator according to claim 1, comprising:
the CPU configured to control a display, wherein
in a case where the pixel value does not reach the target pixel value or the predicted duration does not reach the target duration in a result of the re-simulation, the CPU displays a simulation condition correction proposal.

4. A simulator according to claim 1, wherein
the CPU causes a memory to store a used injection protocol which is used in the simulation and corresponds to a simulation result showing a smallest difference between the target duration and the predicted duration out of the re-simulation results.

5. A simulator according to claim 1, wherein
the CPU causes a memory to store a used injection protocol which is used in the simulation and corresponds to a simulation result showing that the predicted duration is longer than or equal to the target duration and the used amount of the contrast medium is smallest out of the re-simulation results.

6. A simulator according to claim 1, comprising:
the CPU configured to control a display, wherein
the CPU displays the used amount of the contrast medium injected in the injection protocol.

7. A simulator according to claim 1, wherein
the CPU acquires viscosity, an osmotic pressure ratio, and the used amount of the contrast medium corresponding to a chemical liquid name selected by a user.

8. A simulator according to claim 1, wherein
the tissue includes a kidney, and
the CPU calculates a discharged amount of the contrast medium based on a predetermined discharge speed, subtracts the discharged amount from a simulated amount of the contrast medium in capillaries in the kidney, and simulates the time-dependent change.

9. A simulator according to claim 8, wherein
the tissue includes a ureter, and
the CPU allocates the discharged amount of the contrast medium to the ureter and simulates the time-dependent change.

10. A simulator according to claim 1, wherein
the CPU simulates the time-dependent change in each of a plurality of compartments obtained by dividing the tissue along a blood flow direction.

11. An injection device comprising:
an injection head configured to inject a contrast medium according to an injection protocol; and
a simulator, wherein
the simulator includes:
a central processing unit (CPU) configured to acquire an amount of contrast medium,
the CPU configured to acquire a target duration which is to be previously set for a target pixel value of a tissue of a subject,
the CPU configured to acquire a contrast medium injection protocol, and
the CPU configured to simulate a time-dependent change in a pixel value in the tissue of the subject based on the injection protocol and the amount of the contrast medium to determine a predicted duration from when the pixel value reaches the target pixel value until the pixel value is not greater than or equal to the target pixel value, and
the CPU compares the predicted duration with the target duration in a simulation procedure, in a case where the predicted duration is shorter than the target duration, calculates an increase amount by multiplying a difference of the target duration and the predicted duration with a weighting coefficient and re-simulates the time-dependent change in a condition where a first amount of the contrast medium, which is obtained by adding the increase amount to a used amount of the contrast medium used in the simulation, is injected to redetermine the predicted duration, and in a case where the predicted duration is longer than the target duration, calculates a decrease amount by multiplying the difference of the target duration and the predicted duration with the weighting coefficient and re-simulates the time-dependent change in a condition where a second amount of the contrast medium, which is obtained by subtracting the decrease amount from the used amount of the contrast medium, is injected to redetermine the predicted duration.

12. An imaging system comprising:
a medical imaging device configured to capture an image of a subject and selected from a group consisting of a magnetic resonance imaging device, a computed tomography device, an angiographic imaging device, a positron emission tomography device, a single photon emission computed tomography device, a CT angiographic device, an MR angiographic device, an ultrasonic diagnosis device, and a blood vessel imaging device; and
a simulator, wherein
the simulator includes:
a central processing unit (CPU) configured to acquire an amount of contrast medium,
the CPU configured to acquire a target duration which is to be previously set for a target pixel value of a tissue of a subject,
the CPU configured to acquire a contrast medium injection protocol, and
the CPU configured to simulate a time-dependent change in a pixel value in the tissue of the subject based on the injection protocol and the amount of the contrast medium, to determine a predicted duration from when the pixel value reaches the target pixel value until the pixel value is not greater than or equal to the target pixel value, and
the CPU compares the predicted duration with the target duration in a simulation procedure, in a case where the predicted duration is shorter than the target duration, calculates an increase amount by multiplying a difference of the target duration and the predicted duration with a weighting coefficient and re-simulates the time-dependent change in a condition where a first amount of the contrast medium, which is obtained by adding the increase amount to a used amount of the contrast medium used in the simulation, is injected to redetermine the predicted duration, and in a case where the predicted duration is longer than the target duration, calculates a decrease amount by multiplying the difference of the target duration and the predicted duration with the weighting coefficient and re-simulates the time-dependent change in a condition where a second amount of the contrast medium, which is obtained by subtracting the decrease amount from the used amount of the contrast medium, is injected to redetermine the predicted duration.

* * * * *